United States Patent [19]

Van Pool et al.

[11] Patent Number: 4,490,563

[45] Date of Patent: Dec. 25, 1984

[54] ETHER RECOVERY

[75] Inventors: Joe Van Pool; Paul D. Hann, both of Bartlesville, Okla.

[73] Assignee: Phillips Petroleum Company, Bartlesville, Okla.

[21] Appl. No.: 464,819

[22] Filed: Feb. 8, 1983

Related U.S. Application Data

[63] Continuation of Ser. No. 297,456, Aug. 28, 1981, abandoned.

[51] Int. Cl.$^3$ .............................................. C07C 41/58
[52] U.S. Cl. ................................... 568/697; 568/699; 585/331; 585/723; 203/14; 203/46; 203/41
[58] Field of Search ................. 568/697, 699; 585/331, 585/723; 203/46, 14, 41

[56]  References Cited

U.S. PATENT DOCUMENTS 3,726,942  4/1973  Londer .
3,846,088 11/1974  Brown et al. .
4,198,530  4/1980  Wentzheimer et al. .
4,270,929  6/1981  Vu et al. .
4,302,298 11/1981  Mikitenko et al. .

FOREIGN PATENT DOCUMENTS 1369889 10/1974 United Kingdom .
2049693 12/1980 United Kingdom .
2047706 12/1980 United Kingdom .

OTHER PUBLICATIONS

Kirk-Othmer-Encyclopedia of Chemical Technology, John Wiley, New York, 2nd Ed., pp. 381, 393, 1965.

*Primary Examiner*—Howard T. Mars

[57]  ABSTRACT

MTBE is recovered from an ether containing effluent by fractionation. When driers are not used on the hydrocarbon feed to MTBE manufacture, a separate water-methanol phase occurs in the fractionation overhead which is separately processed in a methanol fractionator and the water recovered is used to water wash the separated hydrocarbon phase from the overhead while methanol is recycled to MTBE and when driers are used on the hydrocarbon feed a separate methanol phase occurs in the fractionation overhead which can be recycled to MTBE manufacture and the hydrocarbon phase is directly passed to a drier preceding alkylation.

4 Claims, 1 Drawing Figure

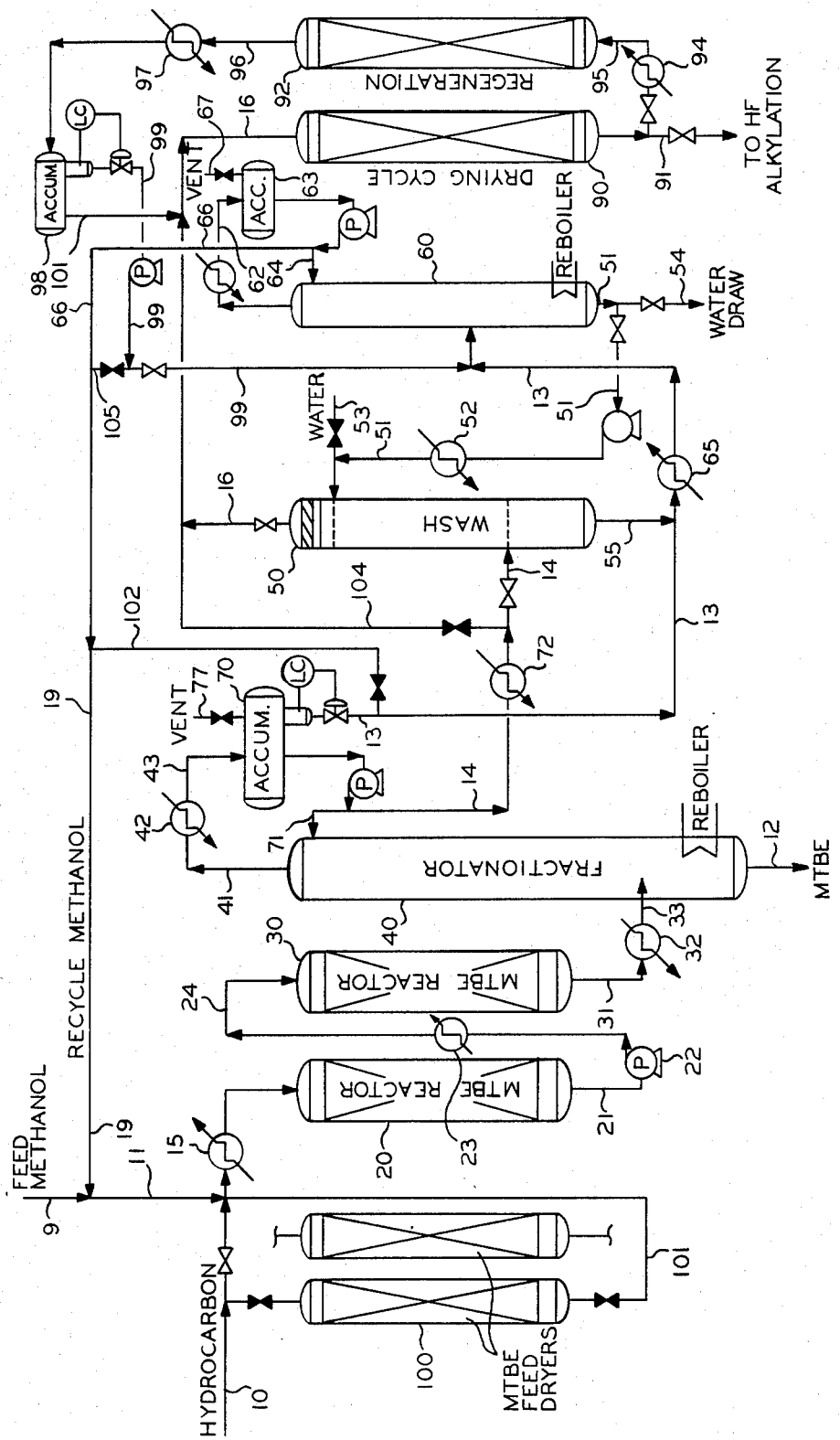

4,490,563

ETHER RECOVERY

This application is a continuation of application Ser. No. 297,456, filed Aug. 28, 1981, now abandoned.

FIELD OF THE INVENTION

This invention relates to the preparation of ethers. In accordance with another aspect, this invention relates to a process for the recovery of ethers especially methyl-tert-butyl ether (MTBE). In accordance with a further aspect, this invention relates to an ether recovery system when driers are not used on the hydrocarbon feed to MTBE manufacture. In a further aspect, this invention relates to an ether recovery system when driers are used on the hydrocarbon feed to MTBE manufacture. In still another aspect, this invention relates to a combination process for the recovery of ethers and unreacted materials, the hydrocarbon portion of which can be passed to alkylation.

BACKGROUND OF THE INVENTION

Methyltertiarybutyl ether (MTBE) is well-known as a high octane blending component for motor fuels. The well-known reaction of methanol (MeOH) and isobutylene, using an appropriate catalyst, such as Amberlyst 15, has been practiced to produce MTBE. Reference is had to U.S. Pat. Nos. 4,071,567; 3,979,461; 3,135,807; 3,846,088; among many others.

HF catalytic alkylation of isobutane with olefins, such as propylene and/or butylenes, is also a well-known process for producing high octane motor fuel. In HF alkylation it is also known that too much water in HF catalyst can adversely affect the alkylation operation, including presenting problems of equipment corrosion. In addition, methanol is not wanted to be present in HF alkylation since methanol uses isobutane in its reaction therewith to produce undesired low octane, high volatility five carbon-atom hydrocarbons and water, the water undesirably diluting the HF catalyst.

Since there is some unreacted methanol and there is some unreacted isobutylene in the MTBE reactor effluent, it is desired to recover these components and to recycle the methanol, preferably, back to the MTBE reaction; and to recover the unreacted isobutylene (along with isobutane and straight chain butylenes, which hydrocarbons are present in the feed to MTBE and act as desired diluents in the MTBE reaction) and charge this recovered isobutylene, freed from methanol, to the HF alkylation.

It is desired that no methanol be yielded, and thereby lost, in the MTBE product. It is desired that substantially no water and no methanol be charged to the HF alkylation.

This invention presents a system: to produce MTBE from methanol and isobutylene with the MTBE being recovered free of methanol and water; to recover methanol and unreacted hydrocarbons; to separate a water and methanol phase from the unreacted hydrocarbons; to water-wash the unreacted hydrocarbons to remove the last traces of methanol therefrom; and to dry these water-washed hydrocarbons prior to charging the methanol-free, water-free hydrocarbons to HF alkylation; to fractionate the water-methanol phase, above-referred-to, to recover substantially pure methanol which can be recycled to MTBE manufacture; and to use the water separated from the methanol as at least part of the water used in the water-wash step, above-referred-to.

OBJECTS

Accordingly, an object of this invention is to provide a process for preparing and recovering ethers.

Another object of this invention is to recover unreacted materials for recycle following an ether reaction.

A further object of this invention is to recover unreacted hydrocarbons in an ether effluent for further use in an alkylation process.

Other objects, aspects, as well as the several advantages of the invention will be apparent to those skilled in the art upon reading the specification, the drawing and the appended claims.

SUMMARY OF THE INVENTION

In accordance with the invention the reaction effluent from a methyl-tert-butyl ether (MTBE) reaction containing MTBE, unreacted $C_4$ hydrocarbons, alcohol, and water, if any, is fractionated to yield an overhead containing $C_4$ hydrocarbons, alcohol, and water, and a bottoms product comprising MTBE, condensing and phase separating the condensed overhead into a hydrocarbon phase and an alcohol phase. The alcohol phase, e.g., methanol, is recycled to the MTBE reaction or passed to a fractionation zone to remove water if water content is excessive. A portion of the hydrocarbon phase, e.g., butenes, is recycled as reflux to the fractionation and the remainder is water-washed, if necessary, to remove alcohol, e.g., methanol, and passed to alkylation.

DESCRIPTION OF THE INVENTION

When driers are not used on the hydrocarbon feed to MTBE manufacture, a separate water-methanol phase can occur in the MTBE fractionator overhead accumulator. This heavier aqueous phase cannot be recycled to the MTBE fractionator because the bottom product MTBE will be then contaminated with methanol and water. This aqueous phase is separately processed in a methanol fractionator to recover methanol for recycle to MTBE and to recover a water stream used to water-wash the separate hydrocarbon phase from this overhead accumulator to remove the methanol therefrom.

When driers are used on the hydrocarbon feed to MTBE manufacture, with sufficient methanol in the feed charged to the MTBE fractionator, a separate methanol phase can occur in the MTBE fractionator overhead accumulator. This methanol liquid phase cannot be recycled to this fractionator because it will allow methanol to be in the bottom MTBE product, contaminating the MTBE, and causing a recovery problem or loss of methanol. This liquid methanol phase from the accumulator can be passed back to the MTBE manufacturing step. The separate accumulator hydrocarbon phase liquid containing methanol can by-pass the water-wash column and can be charged to the feed driers for HF alkylation, wherein the methanol is adsorbed, yielding methanol-free hydrocarbons (also water-free because of the feed driers on the charge to MTBE manufacture) which are charged to HF alkylation. A portion of the hydrocarbon product from the on-stream drier can be heated and vaporized, and used to desorb methanol from that drier on regeneration. The vaporous effluent from this regeneration is condensed and phase separated, with the methanol phase being recycled to MTBE manufacture, and the hydrocarbon phase being recycled to the on-stream drier. In this operation, both the water-wash column and the methanol fractionator can be by-passed.

When MTBE feed driers are used and when insufficient methanol is present in the MTBE reactor effluent to form a separate liquid phase in the MTBE fractionator overhead accumulator, the yield from the accumulator is charged to the HF alkylation feed driers, as described hereinabove, by-passing the water-wash column. Also, the methanol fractionation is not needed for this operation.

It is pointed out that when driers are not used on the feed to MTBE and when the methanol-water phase occurs in the MTBE fractionator overhead accumulator, that the hydrocarbon phase has both water and methanol therein, and after water washing this stream, the washed hydrocarbon is passed to the HF alkylation feed driers. The drier on regeneration can use heated, vaporized dried hydrocarbon for regeneration, and the vapor effluent, hydrocarbon and water, with a trace of methanol, is passed via condensing to a phase separator. The hydrocarbon phase from this accumulator or separator is returned to that drier on the drying cycle, and the aqueous phase is charged to the methanol fractionator, recovering methanol for recycle to the MTBE manufacture.

Given the foregoing description, one skilled in the art having studied the same can determine by mere routine testing the design and conditions of operation required to carry out the invention. However, to more fully describe the invention and to set forth a now best mode contemplated for it in its application to the recovery of the effluent from an ether operation reference is had to the drawing.

Referring now to the drawing, and operating without driers on the hydrocarbon feed to MTBE manufacture, hydrocarbon feed 10, comprising reactant isobutylene and non-reactant, or diluent, isobutane, straight chain butylenes, and normal butane from the field, as from a catalytic cracking operation, is admixed with methanol (feed 9 and recycle 19) added via 11, and the mass is passed via heater 15 to MTBE reactor 20 containing Amberlyst 15 catalyst or other suitable catalyst. Effluent 21 from reactor 20 is pumped 22 via indirect heater 23 and conduit 24 into the second reactor 30, also containing Amberlyst 15 catalyst.

Effluent 31 from reactor 30 is indirectly heated at 32 and passed via conduit 33 to reboiled and refluxed MTBE fractionator 40. MTBE product, substantially free of methanol, is recovered at 12 for use, for example, as a high octane blending component in motor fuel. The overhead vapor stream 41 from fractionator 40 is indirectly cooled and substantially all condensed in 42 and passed via 43 to accumulator 70. Inerts can be removed from accumulator 70 via conduit 77.

In accumulator 70 two liquid phases are formed. The lower liquid phase comprises water and unreacted methanol. The upper liquid phase comprises unreacted hydrocarbons and contains some water and unreacted methanol. The lower liquid phase is passed via conduit 13 and indirect heater 65 to methanol fractionator 60 as part of the feed thereto. The upper hydrocarbon phase from accumulator 70 in part refluxes column 40 via conduit 71, and the yield portion of hydrocarbon phase is passed via conduit 14 and indirect cooler 72 to water wash column 50 wherein the liquid hydrocarbon containing some methanol is washed with liquid water added to the wash column 50 via conduit 51.

Water, containing substantially no methanol, from methanol fractionator 60 is passed via conduit 51 and is pumped via indirect cooler 52 to water wash column 50. Makeup water can be added at conduit 53. Yield water can be removed at conduit 54. Water containing methanol is passed from column 50 via conduit 55 into methanol fractionator 60 along with the material in conduit 13.

Hydrocarbon, substantially freed of methanol but containing solution water (which will also contain some methanol), is recovered at conduit 16 and passed to the HF alkylation feed drier 90 which is on the drying cycle. The dried, methanol-free hydrocarbon is charged via conduit 91 to an HF alkylation, not shown, to effect alkylation of isobutane with propylene and/or butylenes, some of which olefins are present in stream 91. Outside isobutane and propylene and/or butylenes can also be charged to the HF alkylation.

Drier 92 is on the regeneration cycle, preferably using as regeneration fluid a portion of the dried hydrocarbon from drier 90 passed via indirect heater-vaporizer 94 and conduit 95 through drier 92 for regeneration. Vaporous effluent 96 from drier 92 is condensed in exchanger 97 and passed to liquid phase separator 98. The lower aqueous phase (methanol and water) is (pumped) passed via conduit 99 to the methanol fractionator 60 for recovery of methanol for recycle to MTBE manufacture. The hydrocarbon phase is recycled via conduit 101 and conduit 16 to drier 90 on the hydrocarbon drying cycle.

The overhead vaporous methanol from methanol fractionator 60 is condensed in indirect heat exchange condenser 61 and is passed via conduit 62 to overhead accumulator 63. Liquid methanol refluxes fractionator 60 via 64 and the yield methanol portion is passed via conduits 66 and 19 back to MTBE manufacture. Inerts can be vented from accumulator 63 via conduit 67.

When MTBE hydrocarbon feed drier 100 is used, and the dried hydrocarbon 101 is charged to MTBE manufacture, and when sufficient excess methanol is in the reactor effluent, the lower liquid phase formed in accumulator 70 is substantially only methanol. This methanol can be passed via conduits 102 and 19 for recycle to the MTBE manufacture. It is not recycled to fractionator 40 since this would cause methanol to go out with MTBE product. The upper hydrocarbon phase containing some methanol to be yielded is passed via conduit 14, via conduit 104, and via conduit 16 to the on-stream drier 90 to remove the last traces of methanol from the hydrocarbon. On regeneration of the spent drier 92, the dried hydrocarbon from the on-stream drier 90 is passed via indirect heater-vaporizer 94 through drier 92 for regeneration thereof. Vaporous effluent from drier 92 is condensed in indirect exchanger 97 and is passed to liquid phase separator 98. The lower methanol phase is recycled via conduits 99, 105, and 19 to MTBE manufacture. The upper hydrocarbon phase is returned via conduits 101 and 16 to drier 90, as illustrated in the drawing.

When there is insufficient methanol in the feed 33 to the MTBE fractionator, there is no separate methanol phase formed in the overhead accumulator, and, of course, there need be no flow from the leg of accumulator 70 via conduit 13. The hydrocarbon phase containing methanol in solution (this is the operation using drier 100), this stream is used as reflux 71, in part, and yielded via conduits 14, 104, and 16 to drier 90 for removal of the soluble methanol therefrom.

It is pointed out that fractionator 40 is operated so that substantially no methanol exits the bottom thereof along with product MTBE, but that the methanol azeotropes (overhead) with the light hydrocarbons. Pressures and temperatures other than the specific temperatures and pressures tabulated can be selected by those skilled in this fractionation art.

This fractionator 40 is refluxed with separated liquid hydrocarbon, and not ever with the water-methanol phase, which latter stream would cause methanol and water to exit in part in the MTBE, and then this MTBE stream would have to be treated for water and methanol removal and recovery of methanol.

The driers can use conventional molecular sieve 5A, 13X, or the like. Activated alumina can also be used as the desiccant, as is known in the art. Conventional conditions for drying and regeneration are employed in the driers.

Not all of the valves, pumps, heat exchangers, and control systems are shown on the drawing in order to simplify the drawing. Pertinent controls, valves, exchangers, etc. are illustrated, however.

| Calculated Example | | |
|---|---|---|
| Operating Conditions: | | |
| Reactors: | | |
| (20) Temperature at inlet, °F., | 130 | |
| Temperature at Outlet, °F., | 155 | |
| Pressure at Inlet, psia., | 180 | |
| Catalyst, | Amberlyst 15 | |
| LHSV, v/v/hr$^{(a)}$ | 5 | |
| Isobutyl/Methanol Feed Mol Ratio, | 0.72:1.0 | |
| (30) Temperature at inlet, °F., | 110 | |
| Temperature at Outlet, °F., | 115 | |
| Pressure at Inlet, psia., | 180 | |
| Catalyst, | Amberlyst 15 | |
| LHSV, v/v/hr | 5 | |
| Fractionator (40): | | |
| Temperatures: | | |
| Top, °F., | 122 | |
| Bottom, °F., | 236 | |
| Pressures: | | |
| Top, psia., | 80 | |
| Bottom, psia., | 85 | |
| Water Wash Vessel (50): | | |
| Temperature, °F., | 100 | |
| Pressure, psia., | 120 | |
| Methanol Fractionator (60): | | |
| Temperatures: | | |
| Top, °F., | 169 | |
| Bottom, °F., | 240 | |
| Pressures: | | |
| Top, psia., | 23 | |
| Bottom, psia., | 25 | |
| $(a)$ is volumes of liquid per volume of catalyst per hour | | |
| Accumulator (70) | | |
| Temperature, F., | 109 | |
| Pressure, psia., | 75 | |
| Accumulator (63) | | |
| Temperature, °F., | 164 | |
| Pressure, psia., | 20 | |
| | | Pounds/Hour |
| Flow Rates: | | |
| (10) Hydrocarbon Feed, | | 100,000 |
| Wt. % Isobutylene, 15.5 | | |
| Wt. % Water, | 0.05 | |
| (11) Fresh (Feed) and Recycle Methanol, | | 12,309.5 |
| Wt. % water, | 0.26 | |
| (12) MTBE Product, | | 46,240 |
| Wt. % MTBE | 87.9 | |
| Wt. % Hydrocarbon, 12.1 | | |
| Wt. % Water, | 0 | |
| Wt. % Methanol, | 0 | |

-continued

| Calculated Example | | |
|---|---|---|
| (13) Methanol-Water, | | 325.2 |
| Wt. % Water, | 16.8 | |
| Wt. % Methanol, | 83.2 | |
| (14) Hydrocarbon to Water Wash, | | 65,744.3 |
| Wt. % Water, | 0.083 | |
| Wt. % Methanol, | 0.274 | |
| (16) Hydrocarbon From Water Wash, | | 65,581.3 |
| Wt. % Water, | 0.003 | |
| Wt. % Methanol, | 0.107 | |
| (55) Aqueous Stream, | | 10,231.9 |
| Wt. % Methanol, | 1.89 | |
| (66) Recovered Methanol, | | 458 |
| Wt. % Water, | 1.48 | |
| (51) Aqueous Liquid | | 10,072.8 |
| Wt. % Methanol, | 0.13 | |
| (54) Water Removal, | | 72.8 |
| Wt. % Methanol, | 0.13 | |

$^{(a)}$LHSV is volumes of liquid per volume of catalyst per hour

We claim:

1. A process for recovering MTBE from a reaction effluent containing MTBE, methanol, unreacted hydrocarbons comprising isobutylene and other $C_4$ hydrocarbons, and water which comprises
   (a) fractionating said effluent under conditions which separate an overhead stream comprising unreacted hydrocarbons, methanol and water and a bottoms fraction comprising MTBE substantially free of methanol,
   (b) passing said overhead in (a) directly to a condensation zone and subjecting same to condensing and then phase separating said condensed overhead into an upper hydrocarbon phase also containing some methanol and water and a lower liquid phase comprising methanol and water,
   (c) passing said separated upper hydrocarbon phase to a water wash zone and therein contacting same with water under conditions to recover a hydrocarbon stream substantially freed of methanol and water and a water stream containing methanol;
   (d) passing said water stream in (c) and said lower liquid phase in (b) to a second fractionation zone operated under conditions to separately recover a methanol stream and a water stream;
   (e) passing said hydrocarbon stream in (c) through a drying zone and then to an alkylation zone for contact with an olefin and an alkylation catalyst to form alkylate, and
   (f) using at least a portion of the effluent from the drying zone in (e) to regenerate another drier on regeneration cycle and separating the condensate formed into a hydrocarbon phase which is passed to a drier on drying cycle and a water phase containing methanol which is passed as part of the feed for said second fractionation zone in (d).

2. A process according to claim 1 wherein said methanol stream in (d) is recycled to the reaction to form MTBE and the water stream obtained in (d) is used as at least a portion of the water wash in (c).

3. In a process for the production of MTBE wherein the hydrocarbon feed is passed through driers to remove water prior to being passed to MTBE manufacture, the improved process for recovering MTBE from a reaction effluent containing MTBE, unreacted hydrocarbons comprising isobutylene and other $C_4$ hydrocarbons, and methanol, which consists of
   (a) fractionating said effluent under conditions which separate an overhead fraction comprising unreacted hydrocarbons, methanol, and water, if any, and a bottoms fraction comprising MTBE substantially free of methanol, (b) condensing said overhead and phase separating said condensed overhead into an upper hydrocarbon phase containing methanol and a lower liquid phase comprising substantially methanol, (c) passing said hydrocarbon phase to an onstream drier to remove the last traces of methanol (d) recycling said methanol stream in (b) to MTBE manufacture to form said effluent in (a), and (e) using at least a part of the effluent from an onstream drier in (c) to regenerate a drier on regeneration cycle and condensing the effluent from the drier on regeneration and separating the condensate formed into a hydrocarbon phase which is passed to a drier on drying cycle and methanol which is recycled to MTBE manufacture.

4. A process according to claim 3 wherein sufficient excess methanol is used in the MTBE manufacture and forming an effluent (a) that essentially only methanol is formed as lower liquid phase in (b).

* * * * *